(12) United States Patent
Wu

(10) Patent No.: US 8,215,299 B2
(45) Date of Patent: Jul. 10, 2012

(54) COUNTER FOR METERED DOSE INHALER

(75) Inventor: Wei-Hsiu Wu, Younghe (TW)

(73) Assignee: Synmosa Biopharma Corporation, Taipei (TW)

(*) Notice: Subject to any disclaimer, the term of this patent is extended or adjusted under 35 U.S.C. 154(b) by 289 days.

(21) Appl. No.: 12/768,749

(22) Filed: Apr. 28, 2010

(65) Prior Publication Data

US 2011/0265788 A1 Nov. 3, 2011

(51) Int. Cl.
*A61M 11/00* (2006.01)
(52) U.S. Cl. ............... 128/200.23; 128/200.14; 116/307
(58) Field of Classification Search ............. 128/200.14, 128/200.18, 200.23, 203.15, 203.12, 205.23, 128/203.23; 222/32, 36, 162; 116/311–315, 116/317, 318
See application file for complete search history.

(56) References Cited

U.S. PATENT DOCUMENTS

| | | | | |
|---|---|---|---|---|
| 5,421,482 A * | 6/1995 | Garby et al. | ..................... | 222/36 |
| 5,505,192 A * | 4/1996 | Samiotes et al. | .......... | 128/200.14 |
| 5,871,007 A * | 2/1999 | Clark, Jr. | ................. | 128/200.23 |
| 8,074,643 B2 * | 12/2011 | Scarrott et al. | ........... | 128/200.23 |
| 8,082,873 B2 * | 12/2011 | Nuttall | ........................... | 116/285 |
| 2006/0254581 A1 * | 11/2006 | Genova et al. | ........... | 128/200.23 |
| 2007/0295329 A1 * | 12/2007 | Lieberman et al. | ...... | 128/200.23 |
| 2009/0151721 A1 * | 6/2009 | Spaargaren et al. | ..... | 128/203.12 |
| 2011/0041845 A1 * | 2/2011 | Solomon et al. | ......... | 128/203.12 |

* cited by examiner

*Primary Examiner* — Steven Douglas
(74) *Attorney, Agent, or Firm* — Leong C. Lei

(57) ABSTRACT

A dose counter is provided for coupling with a metered dose inhaler. The dose counter includes a top cover that has a top forming an observation window. The top cover forms an interior space receiving therein a circuit board and an electrical cell supplying electrical power. The circuit board includes a counting circuit and a display screen that is arranged under the window. As such, in the use of the inhaler, depression of the top cover actuates the inhaler and causes the display screen to display the number of times of actuation so as to allow a user to realize the remaining number of times for use of the inhaler thereby improving safety of medication use.

6 Claims, 4 Drawing Sheets

COUNTER FOR METERED DOSE INHALER

(a) TECHNICAL FIELD OF THE INVENTION

The present invention generally relates to an electronic inhaler dose counter with displaying window to clearly showing the number of doses released from a medication containing canister, and more particularly to such a structure applicable to a metered dose inhaler or the likes for releasing a predetermined dose of medication for asthma patients.

(b) DESCRIPTION OF THE PRIOR ART

To administrate the medications correctly in time is the most important thing to keep patients in a healthier condition whether he or she is in an acute or chronic disease status in her or his life. Most medications are in visible forms, such as tablet, capsule, injectable, patches, ointment or cream etc., hence patients will clearly know that they have took the medication after they administer them.

However, an asthma patient is often prescribed with a metered dose inhaler or dry powder inhaler prefilled with certain amount of medication. In addition to routine controller treatment, when the patient experienced exacerbations of asthma, he or she can put the inhaler in front of his or her mouth and press the inhaler to release the dose and inhaled sprayed drug into his or her lungs in order to relive the symptom. However, the existing inhaler does not allow a user to visually identify the residual amount of the medication remaining in the medication canister. Under situations where additional inhaler can be immediately available during the exacerbation of asthma, severe consequences can be avoided, however, if patients cannot immediately get a spared inhaler and no one nearby to help, the patient will be put under a dangerous condition with high mortality.

Conventional metered dose inhalers use chlorofluorocarbons (CFCs) as propellants. Since CFC has low water absorbability, it is a common practice to drop the inhaler into water to roughly identify the residual amount of medication by observing the floating condition of the inhaler. Such a way provides only a rough result of inspection and may not be feasible when the patient is leaving away from home. Further, since CFC is a substance that damages the ozone layer of the atmosphere, although the use of CFC in the inhalers is considered an essential use, yet the conventional CFC propellant based inhalers will eventually be replaced by inhalers using hydrofluoroalkane (HFA) as a propellant.

For the HFA based inhalers, since HFA has a strong water absorbability, to ensure stability of medication, it is often not recommended that an inhaler using HFA as propellant be put in water to identify the residual amount of medication. However, a measure that shows the counts of release of individual doses must be provided to allow an inhaler user to identify the residual amount of medication in order to ensure safety of use of medication.

The current solution in practice to such a problem is to add a mechanical window counter to the plastic mouthpiece or actuator of the inhaler. However, this solution greatly increases the cost of the mouthpiece or actuator and made them cost more than ten times higher of the regular mouthpiece or actuator. Furthermore, such design also caused the additional consumption of plastic materials which in return also caused additional burden to the environment. In addition, due to the smaller size of the counting window and designing limits, it is not easy for those having poor eye sights to read, may lead to incorrect reading or counting of the medication quantity. Apparently, there are drawbacks in association with easy to use and correct reading for the known mechanical inhaler counter.

SUMMARY OF THE INVENTION

The primary objective of the present invention is to provide a separated dose counter for an inhaler, which could clearly displays the numbers of doses of medication used so as to avoid the trouble of getting unexpectedly aware of insufficiency of medication, to allows the resetting or zeroing function for the replacement of new medication canister in order for repeating uses, with which the consumption of plastic materials for making a mouthpiece of the inhaler can be reduced for environmental protection and patient could realized the amount of medication used by just watching the large display screen designed for facilitate reading thereof.

To achieve the above objective, the present invention provides a electronic dose counter for use with a medication canister of inhalers. The does counter is composed of a top cover having a top forming an observation window, a circuit board, a positioning ring, an electrical cell, and a bottom cap. The circuit board forms a counting circuit and a display screen. The display screen is arranged below the window. The circuit board is positioned by the positioning ring and the bottom cap is mounted in a bottom-up manner to hold the electrical cell inside the top cover. As such, the bottom cap mounts the dose counter to a rear end of a medication canister and once the medication canister is depressed and actuated, the display screen shows the number of dose released of the medication canister to allow the user to identify the residual amount of medication in the canister.

In the above-described dose counter of the present invention, an elastic device is arranged between the circuit board and the positioning ring and the elastic device is normally in a released condition.

In the above-described dose counter of the present invention, the top cover forms an opening adjacent to the window for receiving and holding therein a reset button provided on the circuit board.

In the above-described dose counter of the present invention, the counting circuit of the circuit board comprises a micro-controller unit (MCU), a display screen, a reset button, and an increment button, wherein the reset button is arranged on a top side of the circuit board, while the increment button is set on a bottom side of the circuit board to which a projection formed on the positioning ring corresponds in position to be engageable with the increment button.

In the above-described dose counter of the present invention, the MCU of the counting circuit sets a predetermined time period of depression of the increment button to identify an effective count by which the number of count shown in the display screen is incremented by 1.

In the above-described dose counter of the present invention, the reset button of the counting circuit is arranged, in a recessed manner, in a horizontal top surface of the top cover.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
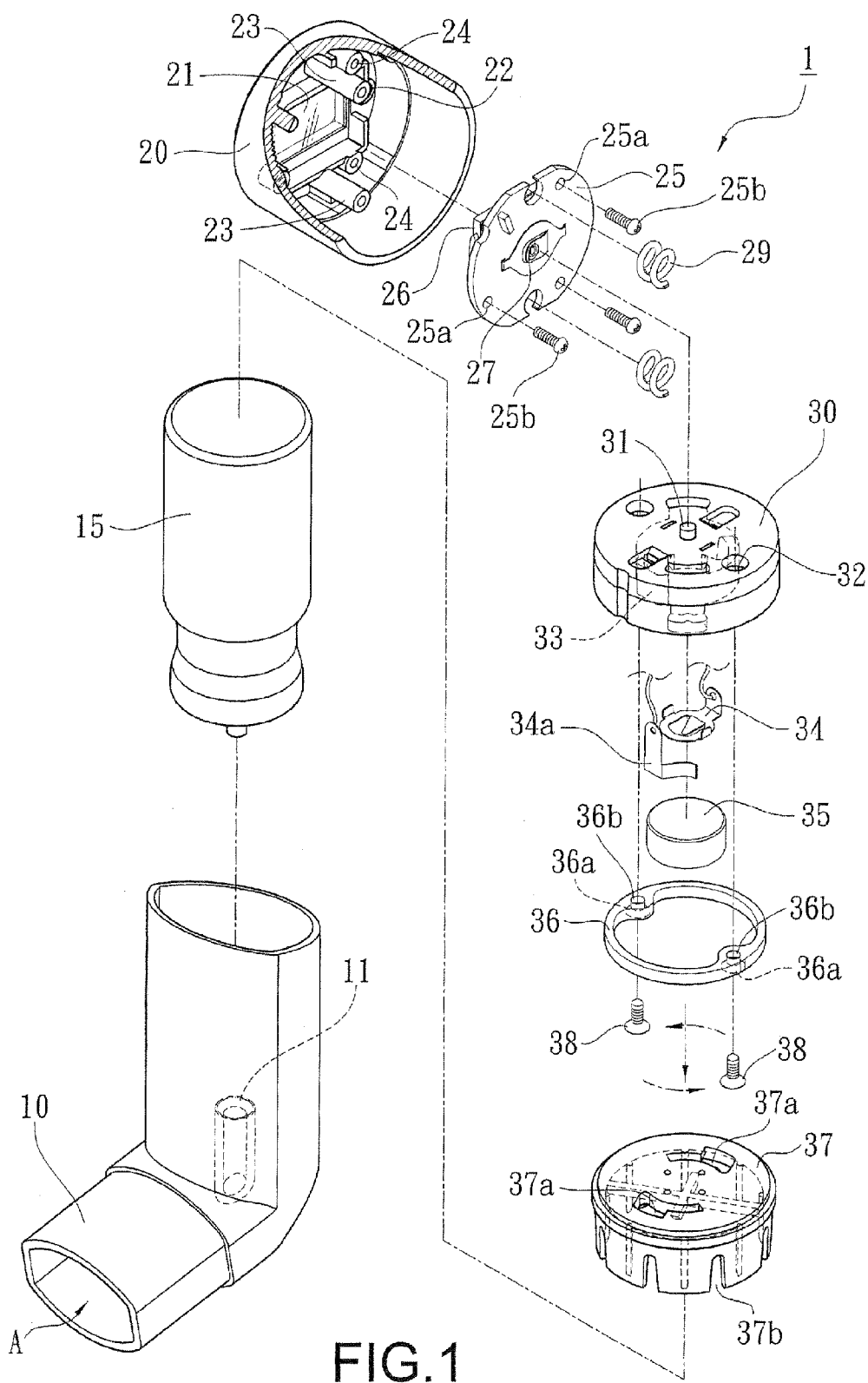
FIG. 1 is an exploded view of an embodiment according to the present invention.
Figure 3:
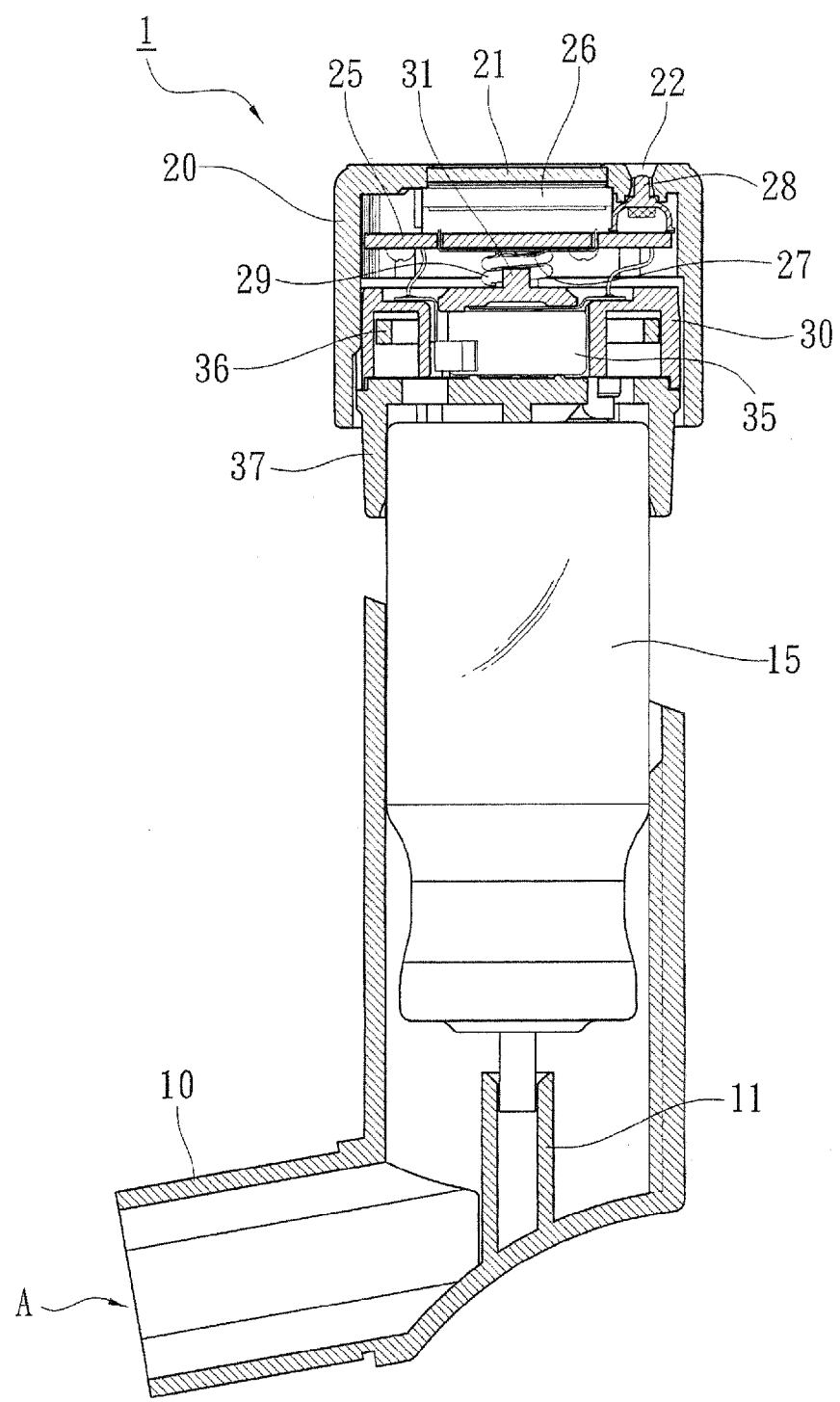
FIG. 3 is a cross-sectional view of the embodiment of the present invention.

Referring to FIGS. 1 and 3, the present invention provides a dose counter, which is generally designated at 1, for an inhaler. The dose counter 1 comprises a top cover 20, a circuit board 25, a positioning ring 30, an electrical cell 35, and a bottom cap 37. The dose counter is installed by fitting the bottom cap 37 to a rear end of a medication canister 15. The medication canister 15 can then installed by fitting a tube formed at a front end thereof into a pump 11 formed in a mouthpiece 10 of the inhaler, whereby the dose counter 1, when depressed for actuation, shows the number of times of actuation by which doses of the medication have been sprayed through the mouthpiece.

The mouthpiece 10 is a known component, showing an L-shaped angled configuration. The mouthpiece has a vertical limb in which the pump 11 (see FIG. 3) is mounted. When the front end tube of the medication canister 15 is fit into and thus coupled to the pump 11, depression can be carried out to cause the medication to be sprayed through an open end. A of the mouthpiece for being inhaled by a patient into the lungs.

Figure 2:
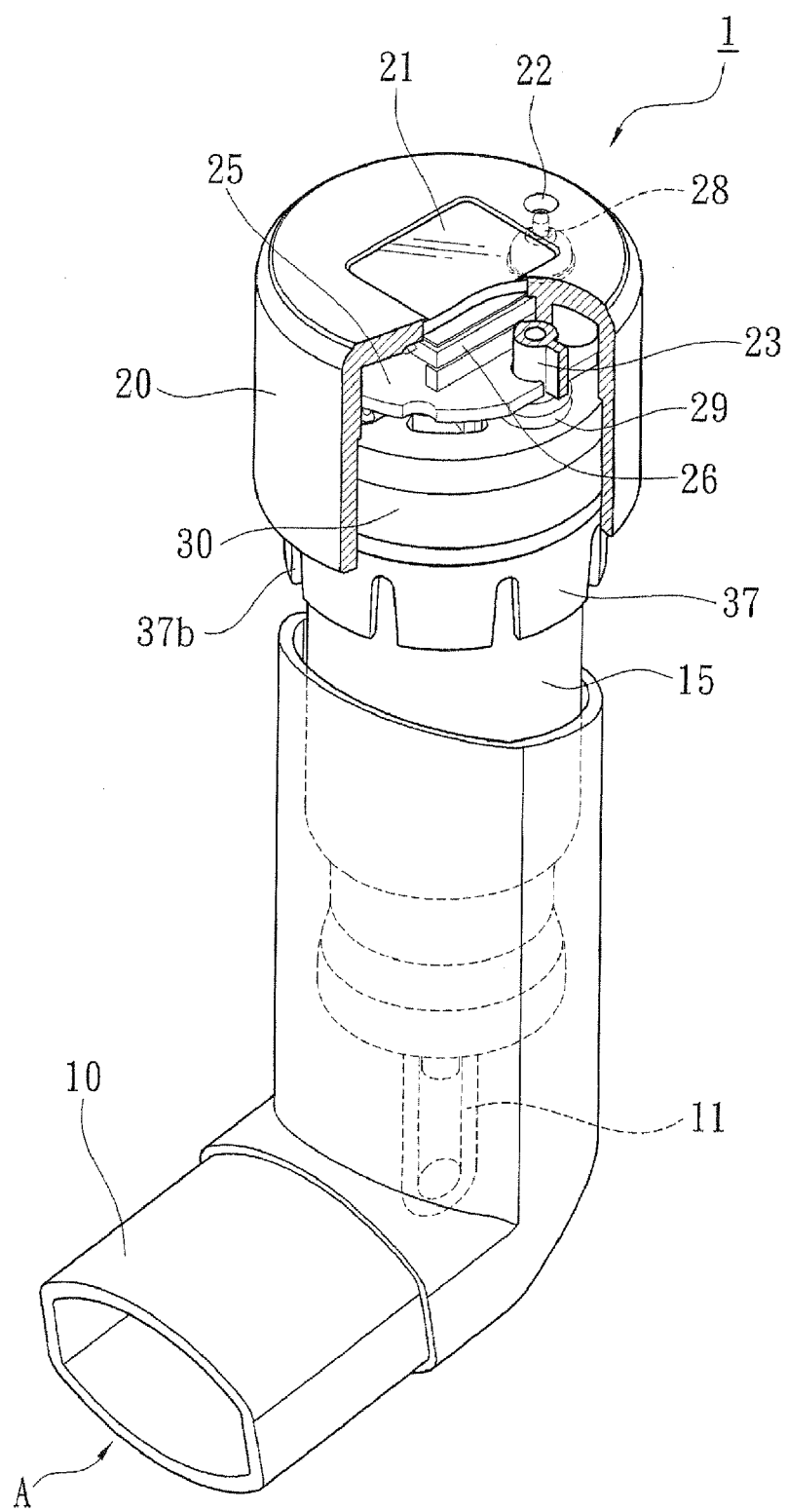
FIG. 2 is a perspective view, partially broken, of the embodiment of the present invention in an assembled form.

Referring to FIG. 2, the top cover 20 is constructed to show an inverted U-shaped cross-section, forming a transparent window 21 in a central portion thereof. An opening 22 is formed next to the window 21. The top cover 20 forms a plurality of coupling holes 24 in an inside surface of. Further, two fixation pegs 23 are formed in a circumferential portion around the window 21 and the two fixation pegs 23 are each provided with an elastic component, which in the embodiment illustrated, comprises a spring 29.

The circuit board 25 carries a counting circuit that is constituted by a micro-controller unit (MCU). The counting circuit is operated with a control parameter of time period of depression or actuation. In the embodiment illustrated, the control parameter is defined as a threshold of time period of depression or actuation, which, when exceeding the threshold, is considered an effective count, with which a display screen 26 increases the total count by one. A preferable preset time period for depression or actuation in this respect is set greater than 0.01 seconds but less than 0.5 seconds to be considered an effective counting signal. Further, the counting circuit comprises a power-saving mode which forces the circuit to enter a sleeping or standby condition when no actuation has been taken for a pre-set time period, such as 30 seconds. The counting circuit is connected to the display screen 26, an increment button 27, and a reset button 28 (see FIG. 3). The display screen 26 and the reset button 28 are arranged on a top face of the circuit board 25, while the increment button 27 is set on a bottom face of the circuit board 25. The circuit board 25 forms a plurality of through holes 25a, through which bolts 25b can be fit to secure the circuit board to the coupling holes 24 formed in the inside surface of the top cover 20.

The positioning ring 30 has a top forming a projection 31, which opposes an underside of the increment button 27. The positioning ring 30 forms through holes 32 corresponding, in position, to the two fixation pegs 23. The positioning ring 30 has a bottom forming an accommodation chamber 33, in which a positive terminal 34 and a negative terminal 34a are mounted. The positive and negative terminals 34, 34a are electrically connected through electrical wires to the circuit board 25. Bolts 38 are set through the through holes 32 to secure the positioning ring 30 to the fixation pegs 23 that have ends forming inner-threaded holes for threading engagement with the bolts. In the embodiment illustrated, the present invention comprises a bottom ring 36, which functions to couple the positioning ring 30 and the bottom cap 37 together.

The bottom ring 36 has a bottom forming retention pins 36a and a top forming through holes 36b. The bolts 38 are put through the through holes 36b of the bottom ring 36 and the through holes 32 of the positioning ring 30 to secure the bottom ring 36 and the positioning ring 30 to the fixation pegs 23.

The bottom cap 37 has a top forming retention slots 37a. The bottom cap 37 comprises a circumferential portion forming a resilient structure 37b, whereby the bottom cap 37 can be coupled to the bottom ring 36 by the retention slots 37 that receive and engage the retention pins 36a of the bottom ring 36, while the resilient structure 37b of the bottom cap 37 allows for secure coupling of the bottom cap to the rear end of the medication canister 15. In an alternative form, the bottom ring 36 is integrally formed with the positioning ring 30 and the bottom cap 37 can then be directly coupled to the positioning ring 30.

Referring to FIGS. 2 and 3, to assemble, the circuit board 25 is set, in a bottom-up manner of moving upward from bottom side, into the top cover 20 with the display screen 26 and the reset button 28 facing upward to have the display screen 26 opposing the window 21 and the reset button 28 received in the opening 22. The bolts 25b are applied to secure the circuit board 25 to the underside of the inside surface of the top cover 20. The springs 29 are then respectively fit over the fixation pegs 23. The positioning ring 30 is set, in a bottom-up manner, to position under the circuit board 25 with the projection 31 faces upward to have the projection 31 in alignment with the increment button 27. The two fixation pegs 23 of the top cover 20, together with the springs 29 fit thereon, are respectively set into the two through holes 32 of the positioning ring 30. The positive and negative terminals 34, 34a of the circuit board 25 are set in the accommodation chamber 33 formed in the bottom of the positioning ring 30 through electrical wires extending from the circuit board. The electrical cell 35 is deposited in the accommodation chamber 33 and the bottom ring 36 is stacked under the positioning ring 30 and secured by the bolts 38. Then, the bottom cap 37 is fit and coupled to the underside of the bottom ring 36. A medication canister 15 can then be installed by having the rear end of the canister fit to the bottom cap 37 and the front end of the canister 15 is fit to the pump 11 of the mouthpiece 10, whereby depression or actuation of the top cover 20 may immediately cause the medication to be sprayed and the number of times of individual doses of the medication that have been sprayed can be shown.

Figure 4:
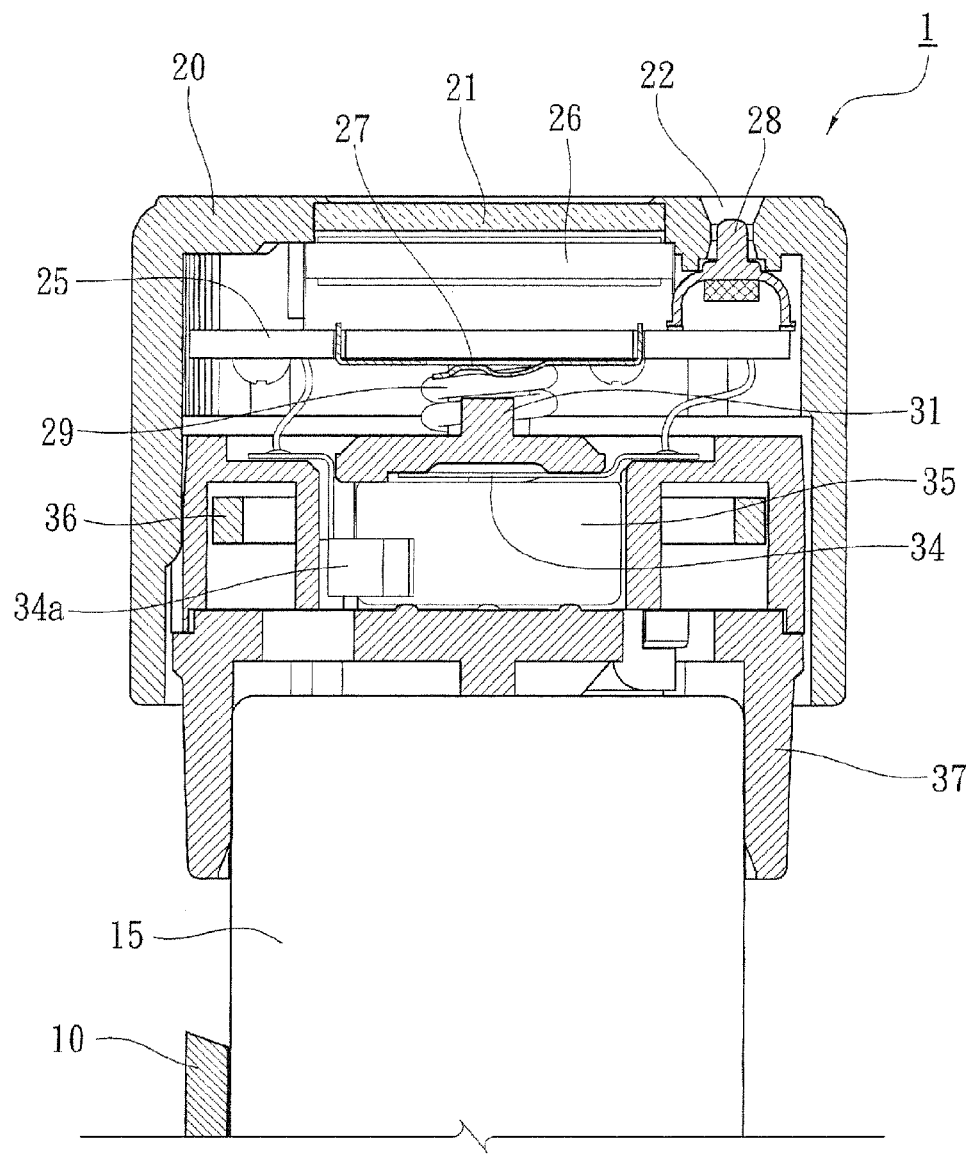
FIG. 4 is an enlarged view of a portion of FIG. 3.

Referring to FIGS. 3 and 4, the dose counter 1 of the present invention uses the bottom cap 37 to couple to the rear end of a medication canister 15, whereby when the medication canister is not put into operation, the springs 29 are in a released condition and resiliently support the circuit board 25 to separate the increment button 27 from the projection 31; and when in use, which is operated by manually depressing the top cover 20, the increment button 27 is indirectly depressed down, causing the counting circuit to resume from the sleeping condition into an actuated condition, or alternatively, in case of replacing a new medication canister and the reset button 28 being triggered, the counting circuit can also be caused to switch from a sleeping condition into an actuated condition. After the display screen 26 is energized to show full illumination for one second, the counter enters a regular operation condition, when the count recorded in the counting circuit is set to zero. When the top cover 20 is depressed to have the increment button 27 on the bottom of the circuit board 25 contacting the projection 31 with the time period of contact therebetween exceeding a threshold, the depression is considered an effective count. In the embodiment illustrated, the depression time is set to be greater than 0.01 seconds and less than 0.5 seconds to be considered an effective count, with which the count of the counting circuit automatically incremented by "1" and the display screen 26 simultaneously shown the digit "1". In this way, successive depression will cause incrementing of the count and the total count of actuation is shown in the display screen 26 by which a user may get aware of the amount of medication remaining in the medication canister 15.

In case that the depression time period of the top cover 20 does not reach the preset range, then it is considered a fault operation and the counting circuit does not count it and the display screen 26 still shows the original number of count.

Further, when the medication canister 15 is used up and replacement of a new canister is required, the top cover of the dose counter according to the present invention is first removed and a sharp article, such as pen tip, is applied to depress the reset button 28 for a long while, so as to reset and zero the original number of counts displayed on the display screen 26. Then, the dose counter is re-set on the new medication canister 15 with the bottom cap 37 and counting can be started again.

In summary, the dose counter according to the present invention makes it possible to clearly show the times of individual dose has been released for a medication canister and thus allows for timely preparation of new medication.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

I claim:

1. A dose counter adapted to install on an end of a medication canister, does counter comprising a top cover, a circuit board, a positioning ring, an electrical cell, and a bottom cap, and characterized in that:

the top cover has a top forming a transparent window, the top cover receiving and retaining therein the circuit board, the positioning ring, the electrical cell, and the bottom cap, an elastic device being arranged between the circuit board and the positioning ring, the circuit board forming a counting circuit that is constituted by a micro-controller unit, the counting circuit being in electrical connection with a display screen, an increment button, and a reset button; and the positioning ring has a top forming a projection, which opposes an underside of the increment button, the positioning ring forming an accommodation chamber, which receives and retains therein positive and negative terminals and the electrical cell, which are electrically connected to the circuit board through electrical conductors, the positioning ring being coupled to the top cover, the bottom cap being coupled to an underside of the positioning ring;

wherein the dose counter is releasably installed on the end of the medication canister with the bottom cap and the medication canister is mounted to a mouthpiece by having an end tube fit into a pump inside the mouthpiece, whereby depression of the dose counter causes the number of times of depression of the dose counter to be displayed.

2. The dose counter according to claim 1, wherein the top of the top cover forms an opening adjacent to the window, the circuit board comprising a reset button in connection with the counting circuit, the reset button being received in the opening.

3. The dose counter according to claim 1, wherein the top cover forms a plurality of coupling holes and the circuit board forms a plurality of through holes, bolts being respectively put through the through holes of the circuit board to secure the circuit board to the coupling holes of the top cover.

4. The dose counter according to claim 1, wherein the top cover forms at least two fixation pegs on a circumferential portion around the window and the positioning ring forms through holes corresponding to the two fixation pegs of the top cover, bolts being respectively put through the through holes to secure the positioning ring to the fixation pegs of the top cover.

5. The dose counter according to claim 1, wherein the positioning ring has a bottom to which a bottom ring is mounted, the bottom ring having a bottom forming retention pins, the bottom ring forming through holes, bolts being respectively put through the through holes of the bottom ring and through holes defined in the positioning ring to couple the bottom ring to the top cover, the bottom cap having a top forming retention slots that receive and engage the retention pins of the bottom ring.

6. The dose counter according to claim 1, wherein the bottom cap has a circumferential portion forming a resilient structure, the resilient structure of the bottom cap being releasably fit to the medication canister.

* * * * *